United States Patent
Oishi et al.

(10) Patent No.: US 8,815,161 B2
(45) Date of Patent: Aug. 26, 2014

(54) GAS SENSOR

(75) Inventors: Hidetoshi Oishi, Saitama (JP); Tsuyoshi Eguchi, Saitama (JP); Takashi Sasaki, Saitama (JP); Akihiro Suzuki, Saitama (JP); Shunji Tsukabayashi, Saitama (JP)

(73) Assignee: Honda Motor Co., Ltd, Tokyo (JP)

( * ) Notice: Subject to any disclaimer, the term of this patent is extended or adjusted under 35 U.S.C. 154(b) by 1251 days.

(21) Appl. No.: 12/014,829

(22) Filed: Jan. 16, 2008

(65) Prior Publication Data

US 2008/0175759 A1 Jul. 24, 2008

(30) Foreign Application Priority Data

Jan. 19, 2007 (JP) .................. 2007-009942

(51) Int. Cl.
*G01N 27/16* (2006.01)
*G01N 7/00* (2006.01)
*G01N 27/12* (2006.01)
*G01N 33/00* (2006.01)
*H01M 8/06* (2006.01)
*H05K 1/14* (2006.01)

(52) U.S. Cl.
CPC ............ *G01N 27/125* (2013.01); *G01N 33/005* (2013.01); *H01M 8/0662* (2013.01); *H05K 1/144* (2013.01)
USPC ................ 422/94; 422/83; 422/95; 422/96; 422/97; 422/98; 73/23.31; 73/25.01; 73/25.05

(58) Field of Classification Search
USPC ........ 73/3.2, 23.31, 24.01, 34.06, 31.05, 570, 73/579, 193, 408; 204/193, 194; 422/98.1, 422/82.01–82.04; 436/43, 149, 150
See application file for complete search history.

(56) References Cited

U.S. PATENT DOCUMENTS

| | | | |
|---|---|---|---|
| 5,897,766 A * | 4/1999 | Kawatsu ........................ 204/426 |
| 2005/0042141 A1 | 2/2005 | Otani et al. |
| 2005/0072212 A1* | 4/2005 | Oishi et al. .................... 73/23.21 |
| 2005/0092065 A1* | 5/2005 | Tajima et al. .................. 73/23.2 |

FOREIGN PATENT DOCUMENTS

| JP | 2004-037235 A | 2/2004 |
|---|---|---|
| JP | 2006-284498 A | 10/2006 |
| JP | 2007-003302 A | 1/2007 |

OTHER PUBLICATIONS

Japanese Office Action dated Mar. 2, 2012, issued in corresponding Japanese Patent Application No. 2007-009942.

* cited by examiner

*Primary Examiner* — Paul Hyun
*Assistant Examiner* — Robert Eom
(74) *Attorney, Agent, or Firm* — Westman, Hattori, Daniels & Adrian, LLP

(57) ABSTRACT

A gas-sensing element configured to measure a concentration of a specific component of a gas is mounted to a first circuit board which includes a driving circuit configured to drive the gas-sensing element. A moisture-proof material is disposed over at least one side of the first circuit board disposed in a tubular gas-sensing element case fixed to a sensor case. A gas-sensing chamber is defined by the first circuit board and an inner tubular surface of the gas-sensing element case, and opens at an open end of the gas-sensing element case to receive the gas to be monitored. A second circuit board which includes a control circuit configured to control the gas-sensing element via the driving circuit is fixed to a sensor case, and disposed in a position separate from the gas-sensing chamber such that the second circuit board is kept out of contact with the gas to be monitored.

14 Claims, 5 Drawing Sheets

GAS SENSOR

CROSS-REFERENCE TO RELATED APPLICATION(S)

This application claims the foreign priority benefit under Title 35, United States Code, §119 (a)-(d), of Japanese Patent Application No. 2007-009942, filed on Jan. 19, 2007 in the Japan Patent Office, the disclosure of which is herein incorporated by reference in its entirety.

BACKGROUND OF THE INVENTION

This invention relates generally to gas sensors, and more particularly to a gas sensor for use, for example, in a fuel cell system.

In general, a polymer electrolyte fuel cell is provided in the form of a fuel cell stack comprised of a plurality of stacked cells each having an anode, a cathode, and a solid polymer electrolyte membrane sandwiched between the anode and the cathode. The anode is supplied with hydrogen as a fuel, and the cathode is supplied with air as an oxidant, so that hydrogen ions produced by catalytic reaction at the anode migrate through the solid polymer electrolyte membrane to the cathode in which the hydrogen ions and the oxygen react electrochemically to generate electricity.

In such a polymer electrolyte fuel cell or other type of fuel cell, generally, unreacted air discharged from the cathode (which is called "exhaust gas") is forced to the outside of the system, and the exhaust gas should be checked, before released to the outside, to ensure that no hydrogen gas is contained therein. Thus, a hydrogen sensor to detect a hydrogen gas is used to monitor the exhaust gas.

Among gas sensors used for such a hydrogen sensor is a gas sensor, as proposed in US 2005/0042141 A1, in which a gas-sensing element is provided in a gas-sensing chamber and a circuit board provided on the outside of the gas-sensing chamber is connected to the gas-sensing element.

If the gas sensor as disclosed in US 2005/0042141 A1 were provided in a relatively high-temperature or relatively high-humidity environment, the heat-resisting and moisture-proof properties of an integrated circuit or microcomputer mounted on the circuit board for control would become matters of grave concern.

There is a need of a gas sensor suitable for use in a high-temperature or high-humidity environment, such as in a fuel cell system. The present invention has been made in an attempt to address the above problems and needs.

Illustrative, non-limiting embodiments of the present invention overcome the above disadvantages and other disadvantages not described above. Also, the present invention is not required to overcome the disadvantages described above, and an illustrative, non-limiting embodiment of the present invention may not overcome any of the problems described above.

SUMMARY OF THE INVENTION

It is an aspect of the present invention to provide a gas sensor comprising a gas-sensing element, a first circuit board, a gas-sensing chamber, and a second circuit board. The gas-sensing element is mounted on the first circuit board and disposed in the gas-sensing chamber. The first circuit board comprises a driving circuit configured to drive the gas-sensing element. The gas-sensing chamber is formed in a case having a first opening through which a gas to be monitored is allowed to enter the gas-sensing chamber and a second opening covered with the first circuit board. The second circuit board comprises a control circuit configured to control the gas-sensing element via the driving circuit. The second circuit board is disposed in a position outside the gas-sensing chamber and a moisture-proof material is disposed to separate the second circuit board and the gas-sensing chamber.

In an exemplary embodiment, the second circuit board may comprise a microcomputer configured to perform an operation based upon a signal output by the gas-sensing element. As such, the second circuit board comprising the control circuit may include a heat-sensitive and/or moisture-sensitive element such as an integrated circuit or microcomputer. In the configuration consistent with the present invention, the second circuit board may be separate from an environment in which the gas is to be monitored and which may be in a high-temperature and/or high-humidity condition, and thus the gas sensor may have a long life without suffering deterioration in its functionality as would otherwise be caused by such an adverse environment that surrounds the second circuit comprising the control circuit.

In another exemplary embodiment, a heater is provided within the gas-sensing chamber, and the second circuit board may comprise a second control circuit configured to control the heater. Optionally, a first temperature sensor may be provided in the gas-sensing chamber, and a second temperature sensor may be provided on the second circuit board, whereas the second circuit board may comprise a second control circuit configured to control the heater based upon comparison between signals output by the first and second temperature sensors.

The above case may comprise a gas-sensing element case and a sensor case.

The gas-sensing element case, gas-sensing element and first circuit board may be combined together to form a subassembly which is mounted to the sensor case, whereas the first circuit board in the subassembly may be communicatively coupled via a communication line with the second circuit board mounted on the sensor case. Here, the subassembly refers to a structural unit assembled separately but designed to be incorporated with other units in the final assembly of a finished product; in this embodiment, at least three components (gas-sensing element case, gas-sensing element and first circuit board) which are supposed to form part of a larger assembly (gas sensor) are assembled beforehand (prior to mounting to the sensor case).

With this construction, a gas-sensing element case in which is disposed a first circuit board (comprising a driving circuit) to which a gas-sensing element is mounted is provided as a subassembly independent of a sensor case to which a second circuit board is mounted and fixed. It is thus possible to easily obtain the characteristics of the gas-sensing element which has not yet been incorporated in the sensor case comprising the second circuit board. As a result, the operating efficiency is improved and the manufacturing process is made flexible and convenient.

Additionally, a heater may be provided within the gas-sensing chamber. The heater may be included in the above subassembly. More specifically, the heater may be included in the above gas-sensing element case. In an exemplary embodiment, the heater may be incorporated in the subassembly. Here, the subassembly refers to a structural unit made up of at least four components (gas-sensing element case, gas-sensing element, first circuit board and heater) which are supposed to form part of a larger assembly (gas sensor) and are assembled beforehand (prior to mounting to the sensor case).

With this construction in which the heater is included in the subassembly independent of the sensor case, it is possible to easily obtain the characteristics of the heater which has not yet been incorporated in the sensor case comprising the second circuit board.

Additionally or alternatively, a temperature sensor may be provided in the gas-sensing chamber. The temperature sensor may be included in the above assembly. More specifically, the temperature sensor may be included in the above gas-sensing element case. Here, the subassembly refers to a structural unit made up of at least four components (gas-sensing element case, gas-sensing element, first circuit board and temperature sensor; plus heater, as the case may be) which are supposed to form part of a larger assembly (gas sensor) and are assembled beforehand (prior to mounting to the sensor case).

With this construction in which the temperature sensor is included in the subassembly independent of the sensor case, it is possible to easily obtain the characteristics of the temperature sensor which has not yet been incorporated in the sensor case comprising the second circuit board. In addition, a second temperature sensor may be provided on the second circuit board.

Additionally or alternatively, a humidity sensor is provided in the gas-sensing chamber. The humidity sensor may be included in the above subassembly. More specifically, the humidity sensor may be included in the above gas-sensing element case. Here, the subassembly refers to a structural unit made up of at least four components (gas-sensing element case, gas-sensing element, first circuit board and humidity sensor; plus heater and/or temperature sensor, as the case may be) which are supposed to form part of a larger assembly (gas sensor) and are assembled beforehand (prior to mounting to the sensor case).

With this construction in which the humidity sensor is included in the subassembly independent of the sensor case, it is possible to easily obtain the characteristics of the humidity sensor which has not yet been incorporated in the sensor case comprising the second circuit board.

In various embodiments of the present invention, the second circuit board fixed to the sensor case may be disposed separate from the gas-sensing element case fixed to the sensor case. The above moisture-proof material may be disposed over at least one side of the first circuit board. The moisture-proof material may preferably but not necessarily be disposed over a side of the first circuit board which faces to the gas-sensing chamber.

In another exemplary embodiment of the present invention, a gas sensor is provided which comprises a sensor case, a subassembly, a second circuit board, and a communication line. The subassembly mounted to the sensor case comprises a tubular gas-sensing element case, a gas-sensing element, and a first circuit board. The gas-sensing element case, which is fixed to the sensor case, has a first open end for receiving a gas to be monitored and a second open end opposite to the first end. The gas-sensing element is configured to measure a concentration of a specific component of the gas. The first circuit board comprises a driving circuit configured to drive the gas-sensing element mounted to the first circuit board. The first circuit board is disposed in the gas-sensing element case a moisture-proof material is disposed over at least one side of the first circuit board. A gas-sensing chamber is defined by the first circuit board and an inner tubular surface of the gas-sensing element case, and opens at the first open end of the gas-sensing element case. The second circuit board which is mounted to the sensor case comprises a control circuit configured to control the gas-sensing element via the driving circuit. The second circuit board is disposed in a position separate from the gas-sensing chamber such that the second circuit board is kept out of contact with the gas to be monitored. Through the communication line, the first circuit board in the subassembly is communicatively coupled with the second circuit board.

BRIEF DESCRIPTION OF THE DRAWINGS

The above and other aspects, further features and advantages of the present invention will become more apparent by describing in detail illustrative, non-limiting embodiments thereof with reference to the accompanying drawings, in which.

DETAILED DESCRIPTION OF THE EXEMPLARY EMBODIMENTS

A detailed description will be given of some exemplary embodiments of the present invention with reference to the drawings. A gas sensor 1 according to one exemplary embodiment of the present invention, as illustrated in FIGS. 1 and 2, may be used in a fuel cell system to measure a concentration of hydrogen, for example, in an exhaust gas pipe 50 (see FIG. 2) through which an exhaust gas discharged from a fuel cell flows, or other space in a fuel cell electric vehicle in which the fuel cell system is installed.

Figure 1:
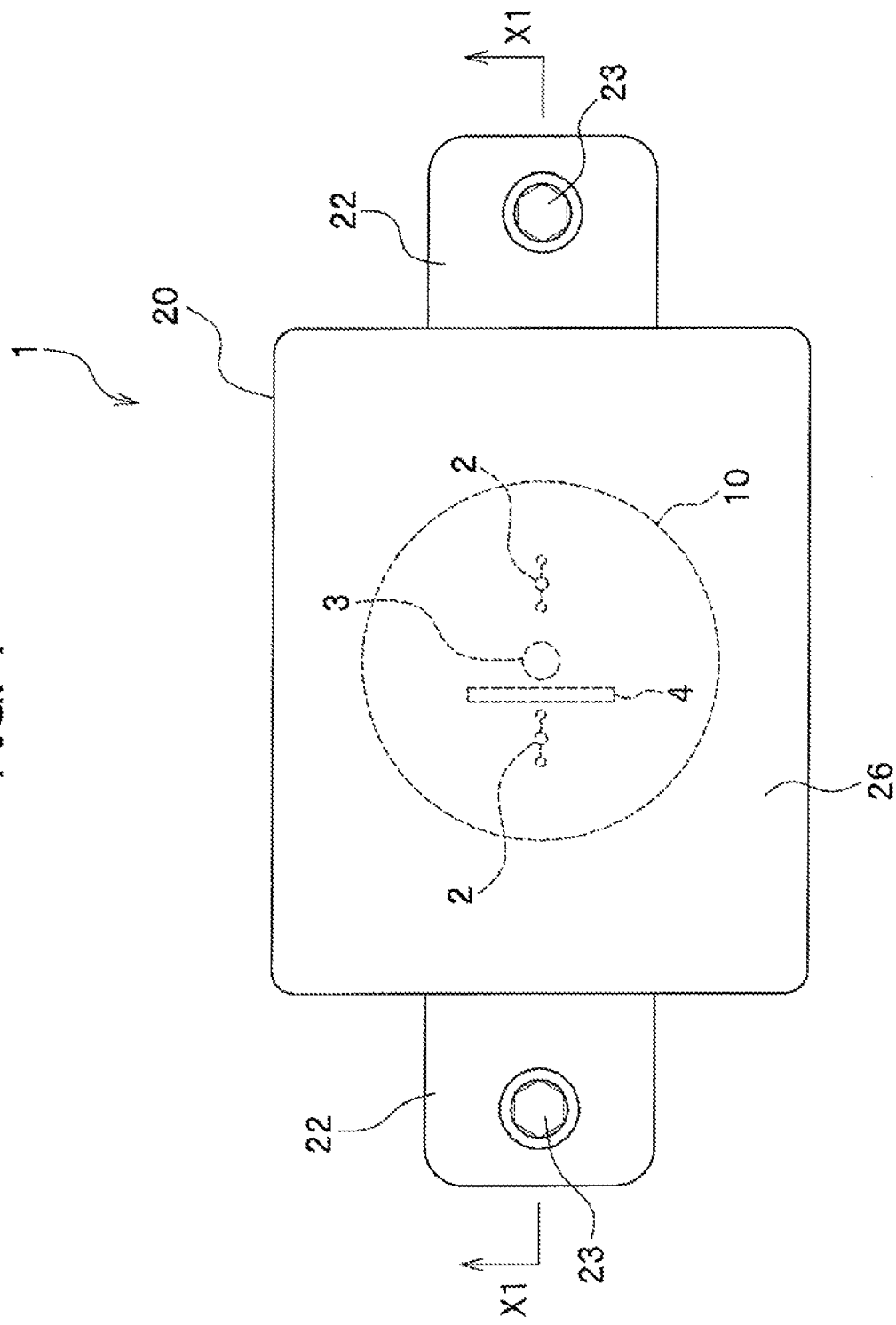
FIG. 1 is a plan view showing a gas sensor according to an exemplary embodiment of the present invention.

As shown in FIG. 1, the gas sensor 1 in the present embodiment includes a gas-sensing element case 10 in which a gas-sensing element driving circuit board 5 (see FIG. 2) is disposed. The gas sensor 1 further includes gas-sensing elements 2, a temperature/humidity sensor 3, and a heat shield plate 4 all of which are mounted to the gas-sensing element driving circuit board 5 and included in the gas-sensing element case 10. The gas sensor 1 further includes a sensor case 20 to which the gas-sensing element case 10 is mounted and fixed. The sensor case 20 may have a tubular shape with a through hole (installation hole) 21 shaped to receive the gas-sensing element case 10; in this embodiment, the installation hole 21 of the sensor case 20 is cylindrically shaped by way of example.

Figure 2:
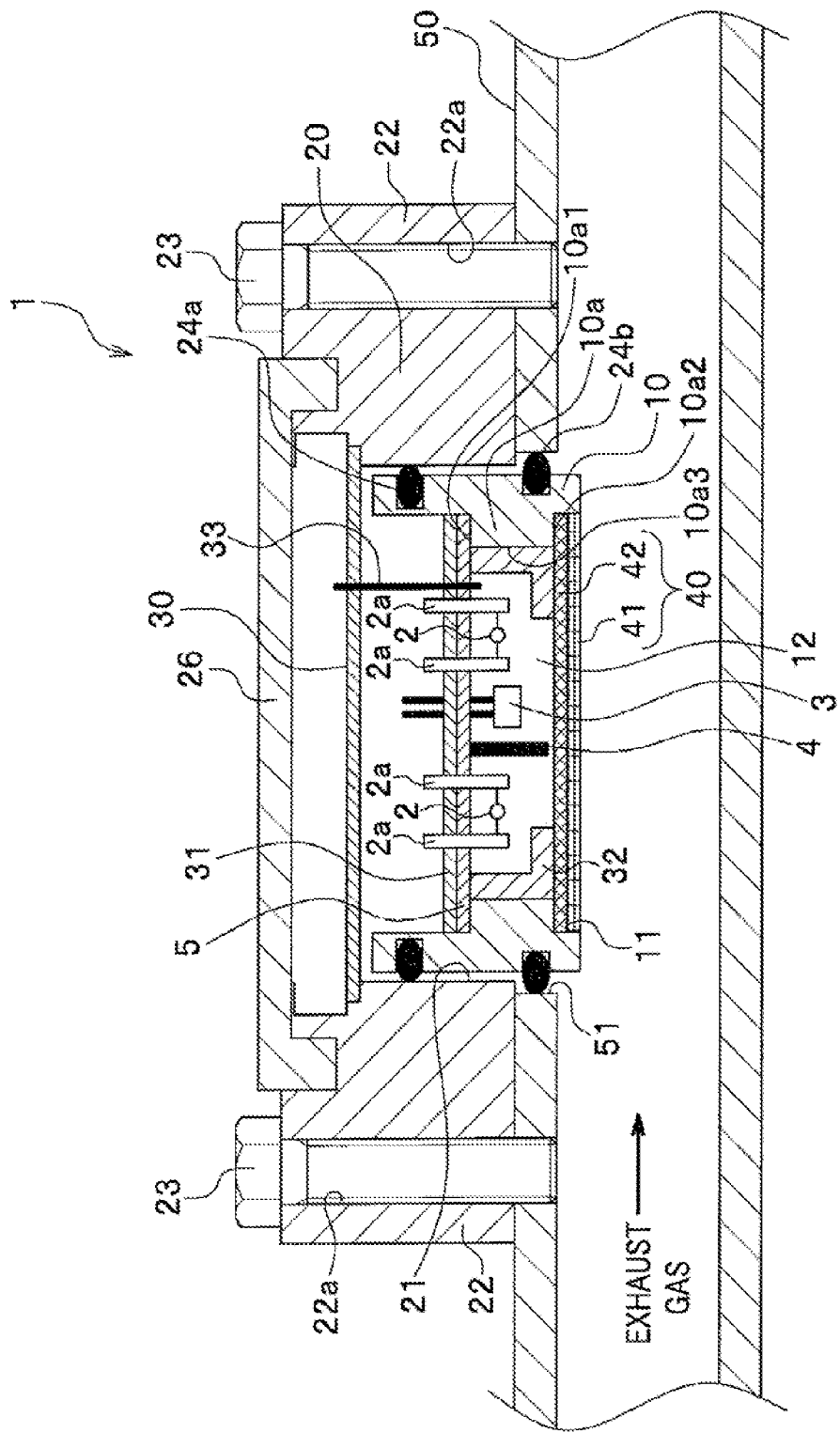
FIG. 2 is a sectional view taken along line X1-X1 of FIG. 1.

As shown in FIG. 2, the gas-sensing element case 10 may also be tubular in shape and sized so as to be fitted into the installation hole 21 and fixed to the inside of the sensor case 20; in this embodiment, the gas-sensing element case 10 has a cylindrical shape having a first open end (lower side in FIG. 2) and a second open end (upper side in FIG. 2) opposite to the first end. The gas-sensing element case 10 has a gas entrance 11 at its first open end to receive a gas to be monitored. The gas-sensing element driving circuit board 5 includes a driving circuit (not shown) configured to drive the gas-sensing elements 2 mounted to the circuit board 5. The gas-sensing element driving circuit board 5 may be disposed at the second open end (upper side in FIG. 2) or some midpoint of the gas-sensing element case 10, though the position of the gas-sensing element driving circuit board 5 consistent with the present invention is not limited to the illustrated embodiment. A gas-sensing chamber 12 is defined by the gas-sensing element driving circuit board 5 and the inner tubular (cylindrical)

surface of the gas-sensing element case 10, and opens at the first open end of the gas-sensing element case 10. Thus, the gas-sensing element driving circuit 5 may be disposed anywhere in the gas-sensing element case 10 as long as an appropriate gas-sensing chamber 12 is provided in which the gas-sensing elements 2 can measure the concentration of a specific component (e.g., hydrogen) of the gas to be monitored (e.g., exhaust gas) received through the first open end (entrance 11) of the gas-sensing element case 10.

The gas-sensing elements 2 are configured to measure the concentration of hydrogen in the exhaust gas flowing through the exhaust gas pipe 50 in this embodiment, and mounted to the gas-sensing element driving circuit 5 and disposed within the gas-sensing chamber 12. To be more specific, each gas-sensing element 2 is supported and connected to the gas-sensing element driving circuit board 5 by a metal stay 2a.

The type, number and arrangement of the gas-sensing elements 2 may be determined according to the method of measuring the concentration of hydrogen. For example, if a catalytic combustible gas sensor is used to measure the concentration of hydrogen, the gas-sensing elements 2 provided in pair comprise a sensing element and a temperature-compensated element. In the gas sensor of this type, hydrogen (gas component to be detected) catalytically burns at the sensing element when it comes in contact with its catalyst such as platinum; thus, the temperature of the sensing element rises relative to the temperature of the temperature-compensated element at which no combustion occurs in the presence of hydrogen (gas component to be detected). Thus-generated difference in temperature between the sensing element and the temperature-compensated element may be represented by a difference in electric resistance. The catalytic combustible gas sensor measures the concentration of hydrogen using such a difference in electric resistance between the sensing element and the temperature-compensated element.

If a semiconductor gas sensor is used to measure the concentration of hydrogen, the gas-sensing elements 2 provided in pair comprise two sensing elements. In the gas sensor of this type, electric resistance changes when hydrogen (gas component to be detected) comes in or out of contact with oxygen adsorbed on the surfaces of the sensing elements. The semiconductor gas sensor measures the concentration of hydrogen based upon this change in electric resistance. The gas-sensing elements 2 may comprise the both of the catalytic combustible gas sensor and the semiconductor gas sensor.

The temperature/humidity sensor 3 is an integral unit of a temperature sensor and a humidity sensor. The temperature/humidity sensor 3 is connected with the gas-sensing element driving circuit board 5 and configured to measure the temperature and humidity of a gas within the gas-sensing chamber 12. The temperature sensor of the temperature/humidity sensor 3 is provided so as to correct the output of sensitivity of the gas-sensing elements 2 when the ambient temperature of the positions in which the gas-sensing elements 2 are disposed changes. To be more specific, since the electric resistances of the gas-sensing elements 2 are subject to variation made according to the ambient temperature, the temperature sensor of the temperature/humidity sensor 3 is configured to provide information for use in canceling the variation of the electric resistances of the gas-sensing elements 2 according to the ambient temperature.

The humidity sensor of the temperature/humidity sensor 3 is provided, when the gas-sensing elements 2 comprise a catalytic combustible gas sensor, to suppress deterioration of the catalyst of the gas-sensing elements 2. To be more specific, since the catalyst provided in the gas-sensing elements 2 of catalyst combustible type would deteriorate with time if it has been exposed to high-humidity conditions for a long time, a heater 32 that will be described later is provided to heat the inside of the gas-sensing chamber 12 in order to keep the catalyst of the gas-sensing elements 2 from taking on moisture. Thus, the humidity sensor of the temperature/humidity sensor 3 is configured to provide information for humidity control in the gas-sensing chamber 12 using the heater 32.

When the gas-sensing elements 2 are of catalytic combustible type, the temperature/humidity sensor 3 may typically be disposed in a position closer to the temperature-compensated element rather than to the sensing element. Sensors which may be provided in the gas-sensing chamber 12 are not limited to the temperature/humidity sensor 3. On the other hand, there may possibly be the case where only the temperature sensor is provided in the gas-sensing chamber 12.

The heat shield plate 4 is a plate member configured to shield radiant heat of the gas-sensing elements 2 (the sensing element and the temperature-compensated element) so that the influence of the heat generated from one gas-sensing element 2 upon the other gas-sensing element 2 is minimized. This heat shield plate 4 is useful particularly for the gas-sensing elements 2 of catalytic combustible type. The heat shield plate 4 may be made of material including, but not limited to, a resin such as polyphenylene sulfide (PPS), polybutylene terephthalate (PBT) or nylon, metal such as aluminum, or the like.

Figure 3:
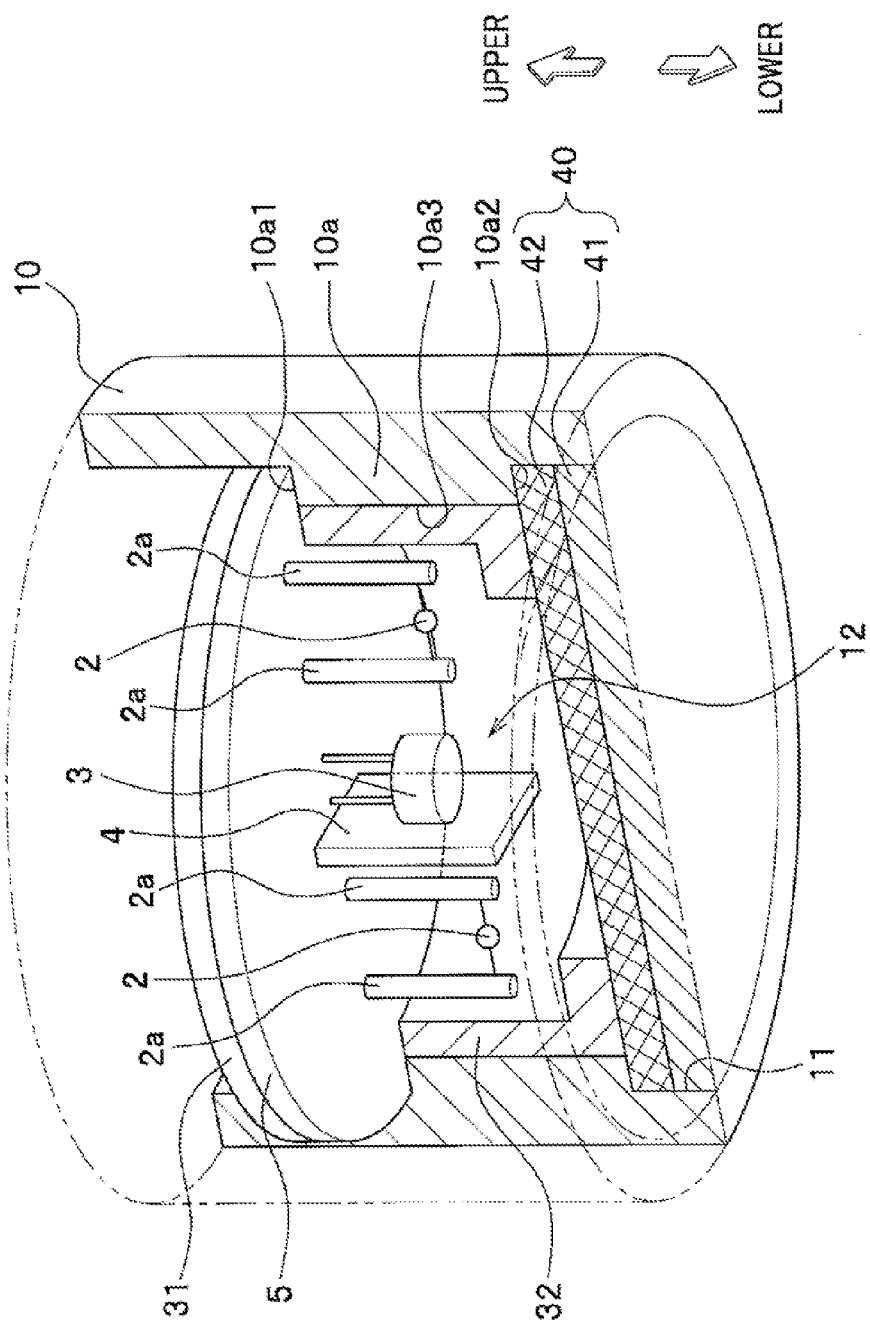
FIG. 3 is a cutaway perspective view showing an inside of a gas-sensing chamber as viewed obliquely from a lower direction.

The gas-sensing element case 10 may be made of material including, but not limited to, a resin such as polyphenylene sulfide (PPS), polybutylene terephthalate (PBT) or epoxy, metal, or the like, and shaped like a cylinder having first and second open ends (lower and upper ends; see FIG. 3). In this embodiment, inner cylindrical surface of the gas-sensing element case 10 is provided with radially inwardly projecting portion 10a shaped like a horizontally and circumferentially extending endless belt having a constant width in the vertical direction (axial direction of its cylindrical shape) and a constant thickness (height of projection) in the radially inward direction thereof. The projecting portion 10a is formed such that an upper end face 10a1 thereof horizontally extends substantially in the middle of the height (vertical dimension) of the gas-sensing element case 10, and a lower end face 10a2 thereof horizontally extends slightly above the lower end of the gas-sensing element case 10.

As shown in FIGS. 2 and 3, at the gas entrance 11 of the gas-sensing element case 10 is provided a laminate 40 of a water-repellent filter 41 and an explosion-proof filter 42. Provided at the lower side facing toward the exhaust gas pipe 50 is the water-repellent filter 41, and provided at the upper side facing toward the gas-sensing chamber 12 is the explosion-proof filter 42. The laminate 40 (water-repellent filter 41 and explosion-proof filter 42) is fitted in the gas-sensing element case 10 with its peripheral edge portion of an upper side kept in contact with the lower end face 10a2 of the projecting portion 10a so that the gas entrance 11 is covered with the laminate 40.

The water-repellent filter 41 is a filter configured to pass a gas to be monitored and to block any liquid contained in the gas, and for example made of tetrafluoroethylene film. The water-repellent filter 41 allows the exhaust gas in gaseous form to enter the gas-sensing chamber 12 while blocking moisture in liquid form contained in the exhaust gas from entering the gas-sensing chamber 12.

The explosion-proof filter 42 is a filter configured to provide an explosion-proof property (capability of withstanding explosion) for the laminate 40, and for example made of metal with a meshed or porous structure through which water in liquid form can be passed.

Provided inside the gas-sensing element case 10 in a position closer to the second open end (on the upper side) than to the first open end (on the lower side) of the gas-sensing element case 10 is the gas-sensing element driving circuit board 5. The gas-sensing element driving circuit board 5 is shaped like a disc to fit the inner cylindrical surface of the gas-sensing element case 10 with its peripheral edge portion of a lower side kept in contact with the upper end face 10a1 of the projecting portion 10a so that the gas-sensing chamber 12 is defined by the gas-sensing element driving circuit board 5 together with the inner cylindrical surface of the gas-sensing element case 10.

The gas-sensing element driving circuit board 5 is composed of a glass epoxy resin substrate or a ceramic substrate, which comprises a driving circuit (not shown) configured to drive the gas-sensing elements 2. On the gas-sensing element driving circuit board 5 are provided a pair of gas-sensing elements 2, temperature/humidity sensor 3, and heat shield plate 4. More specifically, the two gas-sensing elements 2 are disposed separately such that four stays 2a (two in pair) are aligned in a straight line, and the temperature/humidity sensor 3 and the heat shield plate 4 are also aligned in the same straight line between the gas-sensing elements 2. In this embodiment, as illustrated in FIGS. 1 and 2, the temperature/humidity sensor 3 is disposed between the heat shield plate 4 and the gas-sensing element 2 serving as the temperature-compensated element of the catalytic combustible gas sensor.

A layer comprising a moisture-proof material 31 is laminated over a side (upper side in FIG. 2, which is the outside of the gas-sensing chamber 12) of the gas-sensing element driving circuit board 5. This moisture-proof material 31 comprises a material having a moisture-proof property such as epoxy resin, urethane resin, etc., so that the moisture (humidity) in the gas-sensing chamber 12 may not leak through the gas-sensing element driving circuit board 5 to the outside of the gas-sensing chamber 12 particularly to the space in which is disposed a control circuit board 30 that will be described later. The layer comprising the moisture-proof material 31 may not be limited to a layer consisting of such a moisture-proof material alone, but may further comprise a material having a heat-resistant or other property.

A heater 32 is provided in the gas-sensing chamber 12. The heater 32 has a generally annular shape which cylindrically extends over an inner cylindrical surface of a sidewall 10a3 of the projecting portion 10a of the gas-sensing element case 10 and is bent at a lower end of the projecting portion 10a inwardly, so that the heater 32 has a generally L-shaped cross section. The heater 32 is electrically connected to the gas-sensing element driving circuit board 5 via a wire (not shown). Here, the heater 32 applicable to this embodiment may be selected from a positive temperature coefficient heater (PTC heater), a sintered heater, a thin SUS plate heater, a nichrome wire heater, and the like.

When the gas-sensing elements 2 are of catalytic combustible type, heat generated by the heater 32 may not only prevent condensation from forming on the sidewall of the gas-sensing chamber 12, but also heat the gas-sensing elements 2 by conduction, and may further heat the ambient air around the gas-sensing elements 2 so as to prevent condensation from forming around the gas-sensing elements 2

Heating of the gas-sensing chamber 12 by the heater increases the pressure in the gas-sensing chamber 12, and forces the moisture which has once entered the gas-sensing chamber 12 thorough the gas entrance 11 out of the gas-sensing chamber 12, i.e., released into the exhaust gas pipe 50 (see FIG. 2).

The sensor case 20 in this embodiment is made of resin such as polyphenylene sulfide into a substantially rectangular shape as viewed from outside (see FIG. 1), with an installation hole 21 (through hole) provided in the center thereof. Inside the installation hole 21, a control circuit board 30 is installed in a horizontal position. Anchor portions 22 are formed at both sides of the sensor case 20, as shown in FIG. 1, and screw holes 22a (see FIG. 2) are provided in the anchor portions 22. A bolt 23 is inserted in each screw hole 22a, and fastened to the exhaust gas pipe 50 thorough which an exhaust gas is flowed; thereby the gas sensor 1 is fixed to the exhaust gas pipe 50.

The control circuit board 30 comprises a control circuit configured to control the gas-sensing elements 2 via the driving circuit in the gas-sensing element driving circuit board 5. The control circuit board 30 is composed of a glass epoxy resin substrate or a ceramic substrate, in which a microcomputer or the like for generating a signal representative of the concentration of hydrogen measured by the gas sensing elements 2 is incorporated. The microcomputer includes an integrated circuit or the like which is sensitive to moisture and/or heat. As described above, in the gas sensor 1 according to the present embodiment, a microcomputer to be rendered resistant to moisture is included in the control circuit board 30, while no such moisture-sensitive component is included in the gas-sensing element driving circuit board 5. Furthermore, the control circuit board 30 includes a control circuit configured to control the heater 32 based upon information conveyed as a humidity signal from the temperature/humidity sensor 3 for humidity management (e.g., switching control circuit configured to power on or off the heater 32).

The gas-sensing element case 10 in which the gas-sensing element driving circuit board 5 having the gas-sensing elements 2, temperature/humidity sensor 3 and heater 32 as described above mounted thereto, and laminate 40 comprised of the water-repellent filter 41 and the explosion-proof filter 42 are installed is fitted (squeezed) in the installation hole 21 of the sensor case 20 with an O-ring 24a put between the inner cylindrical surface of the sensor case 20 and the outer cylindrical surface of the gas-sensing element case 10, such that the lower end of the gas-sensing element case 10 protrudes slightly from the lower end of the sensor case 20. In the illustrated embodiment, the O-ring 24a is fitted in a groove formed on the outer cylindrical surface of the gas-sensing element case 10 to hermetically seal the annular interstice between the sensor case 20 and the gas-sensing element case 10, so that exhaust gas flowing through the exhaust gas pipe 50 is never allowed to leak through the interstice between the sensor case 20 and the gas-sensing element case 10. Furthermore, the gas-sensing element case 20 is fitted in a round through hole 51 provided in the exhaust gas pipe 50 with an O-ring 24b put between the outer cylindrical surface of the gas sensing element case 20 and the cylindrical sidewall formed around the through hole 51 of the exhaust gas pipe 50, such that the lower end of the gas-sensing element case 10 protrudes slightly into the inside (beyond the interior wall) of the exhaust gas pipe 50 or comes substantially flush with the interior wall of the exhaust gas pipe 50. In the illustrated embodiment, the O-ring 24b is fitted in a groove formed on the outer cylindrical surface of the gas-sensing element case 10 to hermetically seal the annular interstice between the gas-sensing element case 10 and the through hole 51 of the exhaust gas pipe 50, so that the exhaust gas flowing through the exhaust gas pipe 50 is never allowed to leak through the interstice between the gas sensing element case 10 and through hole 51 of the exhaust gas pipe 50.

After the gas-sensing element case 10 in which the gas-sensing elements 2 and other components are installed is mounted to the sensor case 20 as described above, a communication line 33 extending from the gas-sensing element driving circuit board 5 is connected to the control circuit board 30 by means of soldering or the like. Connection between the gas-sensing element driving circuit board 5 and the control circuit board 30 may be established by any means other than soldering, for example, a connector may be employed such that a plug provided at a tip end of the communication line 33 is put in a jack provided on the control circuit board 30.

The sensor case 20 may be provided with a lid 26 which may be placed entirely over the installation hole 21 provided at the upper side of the sensor case 20, so that the installation hole 21 may be hermetically sealed. The lid 26 may be made of PPS resin. Provision of the lid 26 in such a manner as described above may serve to protect the control circuit board 30 against undesirable intrusion of water or the like from outside the gas sensor 1. Alternatively or additionally, the outside (upper side) of the control circuit board 30 may be covered with a coating material such as epoxy resin, which may or may not obviate the necessity of the lid 26.

With the gas sensor 1 implemented according to the present embodiment, the gas-sensing element driving circuit board 5 and the control circuit board 30 is separately provided, and thus the control circuit board 30 which may incorporate a microcomputer or like other heat-sensitive and/or moisture-sensitive component may be separated from high-temperature/high-humidity environments. As a result, the gas sensor 1 may have a long life without suffering deterioration in its functionality.

With the gas sensor 1 implemented according to the present embodiment, after the gas-sensing elements 2, gas-sensing element driving circuit board 5 and gas-sensing element case 10 are subassembled, the gas-sensing element case 10 is mounted to the sensor case 20, so that the gas-sensing element case 10 including the gas-sensing element driving circuit board 5 is provided independent of the sensor case 20 to which the control circuit board 30 is mounted. Accordingly, the gas-sensing elements 2 in the gas-sensing element case 10 that has not yet been mounted to the sensor case 20 may be subjected to calibration of sensitivity to hydrogen (gas component to be detected), to thereby obtain the characteristics of the gas-sensing elements 2. As a result, in comparison with the case where the characteristics of the gas-sensing elements are obtained from a completely assembled gas sensor with the gas-sensing element case 10 mounted to the sensor case 20, the manufacturing cost may be reduced because it is not necessary to discard or recycle the fully assembled gas sensor (but rather it is sufficient to reject a defective subassembly) even if the characteristics thus checked fails to comply with the required level of quality. Hereupon, the characteristics may include the relationship between the concentration of hydrogen (gas component to be detected) and the temperature, the relationship between the temperature and the electric resistance, and the like.

With the gas sensor 1 implemented according to the present embodiment, the heater 32 is mounted together with the gas-sensing elements 2 in the gas-sensing element case 10 to form a subassembly. Thus, the characteristics of the heater 32 may be obtained before the subassembly is mounted to the sensor case 20 to which the control circuit board 30 is mounted. Accordingly, since the characteristics of the heater 32 may be obtained before the gas sensor is completely assembled into a finished product, the manufacturing cost may be reduced for the same reasons as discussed above.

With the gas sensor 1 implemented according to the present embodiment, the temperature/humidity sensor 3 is mounted together with the gas-sensing elements 2 in the gas-sensing element case 10 to form a subassembly. Thus, the characteristics of the temperature/humidity sensor 3 may be obtained before the subassembly is mounted to the sensor case 20 to which the control circuit board 30 is mounted. Accordingly, since the characteristics of the temperature/humidity sensor 3 may be obtained before the gas sensor is completely assembled into a finished product, the manufacturing cost may be reduced for the same reasons as discussed above.

Figure 4:
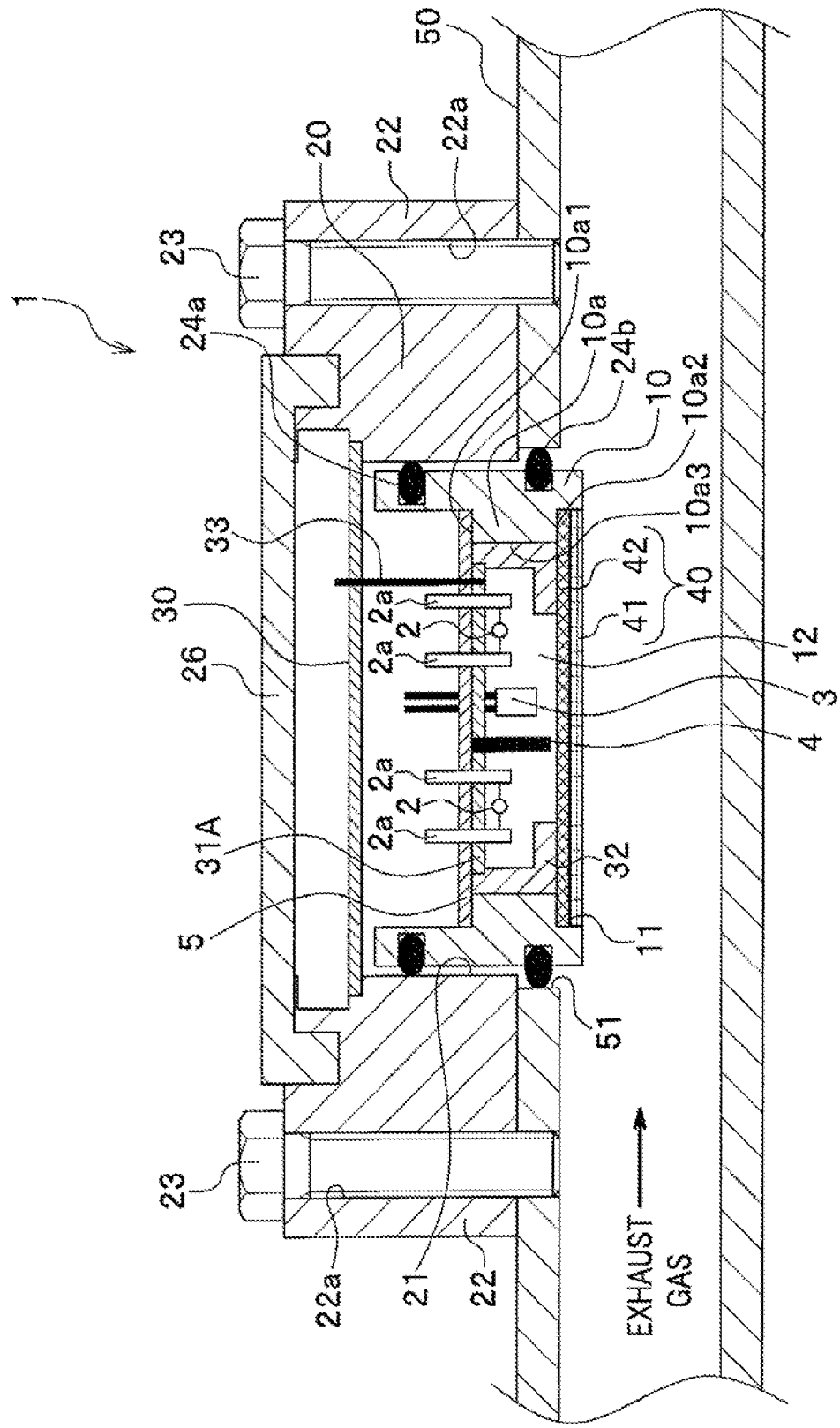
FIG. 4 is a sectional view showing a gas sensor according to a modified embodiment of the present invention.

The present invention is not limited to the illustrated embodiments discussed above. For example, a layer comprising a moisture-proof material 31A may be laminated over a side (lower side, which is the inside of the gas-sensing chamber 12) of the gas-sensing element driving circuit board 5 as shown in FIG. 4. This arrangement where the moisture-proof material 31A is disposed over the side of the gas-sensing element driving circuit board 5 facing toward the gas-sensing chamber 12 makes it possible to protect the gas-sensing element driving circuit board 5 from moisture (humidity), and thus lengthen the life of the gas-sensing element driving circuit board 5 without suffering deterioration in its functionality.

Figure 5:
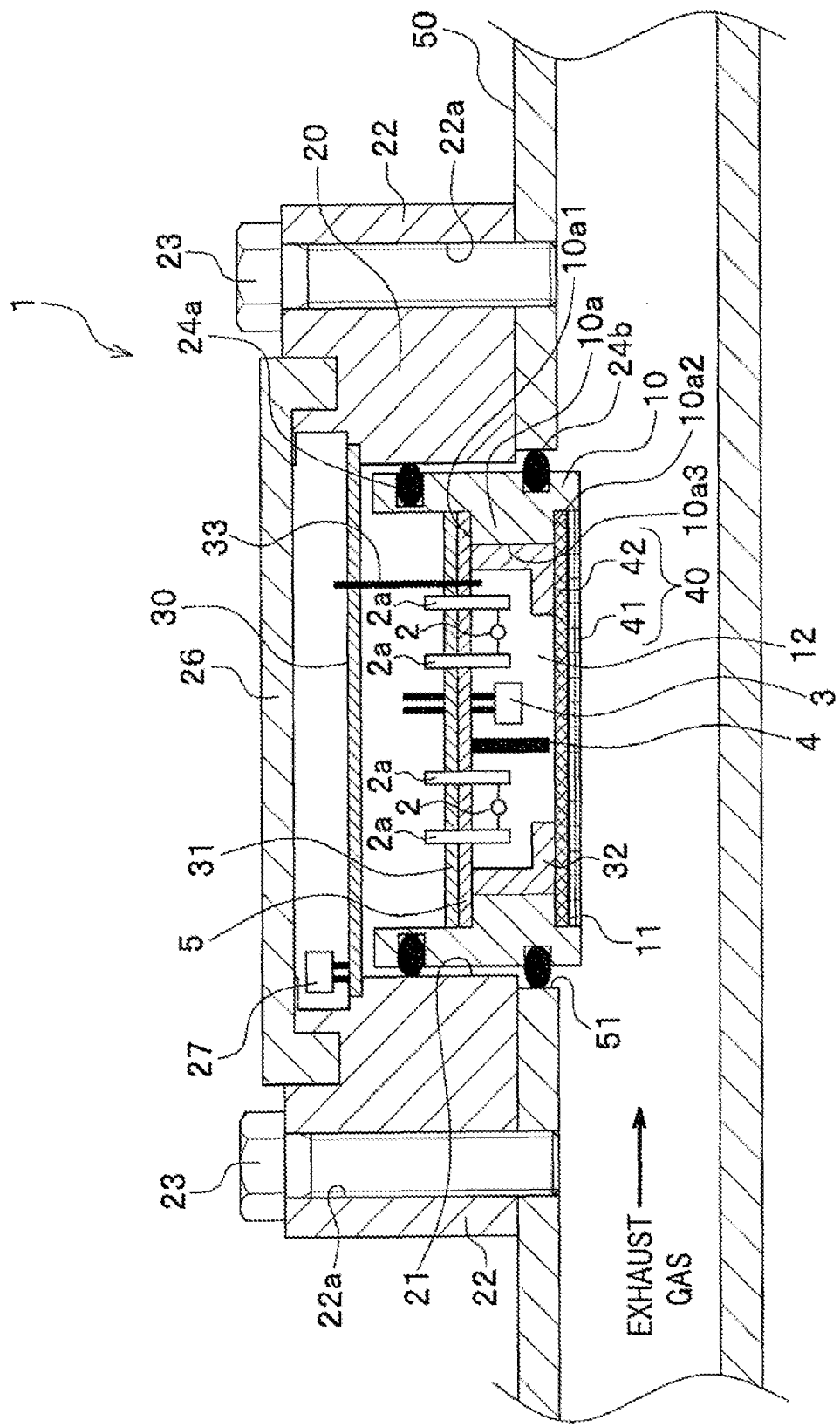
FIG. 5 is a sectional view showing a gas sensor according to another modified embodiment of the present invention.

Furthermore, as shown in FIG. 5, a temperature sensor 27 may be arranged on the control circuit board 30. With this arrangement, the temperature obtained from the temperature/humidity sensor 3 in the gas-sensing chamber 12 may be compared with the temperature obtained from the temperature sensor 27 outside the gas-sensing chamber 12, so that the possibility of condensation in the gas-sensing chamber 12 may be predicted based upon the results of comparison. For example, if the outside temperature obtained from the temperature sensor 27 is significantly higher than the temperature in the gas-sensing chamber 12, then it may be determined that condensation is likely to form inside the gas-sensing chamber 12 and thus proactive control for preventing the condensation may be exercised and the heater 32 may be turned on where appropriate.

It is contemplated that various modifications and changes may be made to the exemplary embodiments of the invention without departing from the spirit and scope of the embodiments of the present invention as defined in the following claims.

What is claimed is:

1. A gas sensor for detecting a hydrogen concentration in an exhaust-gas pipe comprising:
   a first circuit board;
   a gas-sensing element case in which a gas-sensing chamber is formed, the gas-sensing element case having a first opening through which an exhaust gas to be monitored is allowed to enter the gas-sensing chamber and a second opening covered with the first circuit board;
   a sensor case secured to the exhaust gas pipe and including an installation hole, wherein the gas-sensing element case is fixed in the installation hole with an O-ring disposed on and between an inner side surface of the installation hole and an outer side surface of the gas sensing element case;
   a gas-sensing element mounted on the first circuit board and disposed in the gas-sensing chamber, wherein the first circuit board comprises a driving circuit configured to drive the gas-sensing element;
   a second circuit board installed in the installation hole opposite to the first circuit board and comprising a first control circuit configured to control the gas-sensing element via the driving circuit, wherein the second circuit board is disposed in a position outside the gas-sensing chamber and spaced apart from the first circuit board to have a space between the first circuit board and the second circuit board with a moisture-proof material being disposed over the first circuit board and in the space, a first temperature sensor provided in the gas-sensing chamber;

a second temperature sensor provided on the second circuit board; and a heater provided in the gas-sensing chamber, wherein the second circuit board comprises a second control circuit to compare a first temperature from the first temperature sensor and a second temperature from the second temperature sensor to control the heater based upon comparison between the first and second temperature sensors.

2. The gas sensor according to claim 1, wherein the gas-sensing element case, the gas-sensing element, and the first circuit board are combined together to form a subassembly which is mounted to the sensor case, and the first circuit board in the subassembly is communicatively coupled via a communication line with the second circuit board mounted to the sensor case.

3. The gas sensor according to claim 2, wherein the subassembly further comprises the heater.

4. The gas sensor according to claim 2, wherein the subassembly further comprises the first temperature sensor.

5. The gas sensor according to claim 2, further comprising a humidity sensor provided in the gas-sensing chamber, wherein the subassembly further comprises the humidity sensor.

6. The gas sensor according to claim 1, wherein the second circuit board comprises a microcomputer configured to perform an operation based upon a signal output by the gas-sensing element.

7. A gas sensor for detecting a hydrogen concentration in an exhaust-gas pipe comprising:

a sensor case secured to the exhaust gas pipe and including an installation hole;

a subassembly mounted to the sensor case, wherein the subassembly comprising:

a tubular gas-sensing element case fixed in the installation hole with an O-ring disposed on and between an inner side surface of the installation hole and an outer side surface of the tubular gas sensing element case, the tubular gas-sensing element case having a first open end for receiving a gas to be monitored and a second open end opposite to the first end;

a gas-sensing element configured to measure a concentration of a specific component of the gas; and a first circuit board disposed in the tubular gas-sensing element case between the first open end and the second open end such that the first circuit board comprises a first open end side and a second open end side, wherein a gas-sensing chamber is defined by the first circuit board and an inner tubular surface of the gas-sensing element case, and opens at the first open end of the gas-sensing element case, the first circuit board comprising a driving circuit configured to drive the gas-sensing element mounted to the first circuit board, a moisture-proof material being laminated over at least one side of the first open end side and the second open end side of the first circuit board such that a moisture does not leak from the gas-sensing chamber through the first circuit board to the second open end side;

a second circuit board installed in the installation hole opposite to the first circuit board, wherein the second circuit board comprises a control circuit configured to control the gas-sensing element via the driving circuit, the second circuit board being disposed in a position separate from the gas-sensing chamber such that the second circuit board is kept out of contact with the gas to be monitored; and a communication line through which the first circuit board in the subassembly is communicatively coupled with the second circuit board, wherein the second circuit board is disposed on the second open end side of the first circuit board such that the second circuit board is spaced from the first circuit board and the moisture-proof material.

8. The gas sensor according to claim 7, wherein the subassembly further comprises a heater provided within the gas-sensing chamber.

9. The gas sensor according to claim 7, wherein the subassembly further comprises a temperature sensor provided within the gas-sensing chamber.

10. The gas sensor according to claim 7, wherein the subassembly further comprises a humidity sensor provided within the gas-sensing chamber.

11. The gas sensor according to claim 7, wherein the second circuit board mounted to the sensor case is disposed separate from the gas-sensing element case fixed to the sensor case.

12. The gas sensor according to claim 7, wherein the moisture-proof material is disposed over a side of the first circuit board which faces to the gas-sensing chamber.

13. The gas sensor according to claim 9, further comprising a second temperature sensor provided on the second circuit board.

14. A gas sensor for detecting a hydrogen concentration in an exhaust-gas pipe comprising:

a sensor case fixed to the exhaust gas pipe and including an installation hole;

a tubular gas-sensing element case fixed in the installation hole with an O-ring disposed on and between an inner side surface of the installation hole and an outer side surface of the tubular gas sensing element case, the tubular gas-sensing element case having a first open end for receiving a gas to be monitored and a second open end opposite to the first end;

a gas-sensing element configured to measure a concentration of a specific component of the gas; and a first circuit board disposed in the tubular gas sensing element case between the first open end and the second open end such that the first circuit board comprises a first open end side and a second open end side, wherein a gas-sensing chamber is defined by the first circuit board and an inner tubular surface of the gas-sensing element case, and opens at the first open end of the gas-sensing element case, the first circuit board comprising a driving circuit configured to drive the gas-sensing element mounted to the first circuit board, a moisture-proof material being laminated over at least one side of the first end side and the second end side of the first circuit board such that a moisture does not leak from the gas-sensing chamber through the first circuit board to the second open end side;

a second circuit board installed in the installation hole opposite to the first circuit board, wherein the second circuit board comprises a control circuit configured to control the gas-sensing element via the driving circuit, the second circuit board being disposed in a position separate from the gas-sensing chamber such that the second circuit board is kept out of contact with the gas to be monitored; and a communication line through which the first circuit board in the subassembly is communicatively coupled with the second circuit board, wherein the second circuit board is disposed on the second open end side of the first circuit board such that the second circuit board is spaced from the first circuit board and the moisture-proof material.

* * * * *